United States Patent [19]

Zuk

[11] Patent Number: 4,594,327

[45] Date of Patent: Jun. 10, 1986

[54] ASSAY METHOD FOR WHOLE BLOOD SAMPLES

[75] Inventor: Robert F. Zuk, Menlo Park, Calif.

[73] Assignee: Syntex (U.S.A.) Inc., Palo Alto, Calif.

[21] Appl. No.: 548,165

[22] Filed: Nov. 2, 1983

[51] Int. Cl.[4] .................. G01N 33/53; G01N 33/544; G01N 33/557; G01N 33/558

[52] U.S. Cl. ..................................... 436/514; 422/56; 435/7; 435/805; 436/517; 436/520; 436/528; 436/530; 436/541; 436/808; 436/810; 436/825; 436/827

[58] Field of Search .............. 436/514, 517, 528, 530, 436/810, 825, 827, 520, 541, 808; 435/7, 805; 422/56

[56] References Cited

U.S. PATENT DOCUMENTS

| | | | |
|---|---|---|---|
| 3,552,928 | 1/1971 | Fetter | 422/56 |
| 4,168,146 | 9/1979 | Grubb et al. | 435/7 |
| 4,298,688 | 11/1981 | Kallies | 435/14 |
| 4,435,504 | 3/1984 | Zuk et al. | 435/7 |

OTHER PUBLICATIONS

Anderson, Analyt. Biochem. 38 (1970), 175–189.
Metzler, *Biochemistry The Chemical Reactions of Living Cells*, Academic Press, New York, 1977, pp. 281–282.
Glad et al., "Analytical Biochemistry", 116, 335–340 (1981).

*Primary Examiner*—Sidney Marantz
*Assistant Examiner*—Patricia Kate White
*Attorney, Agent, or Firm*—Theodore J. Leitereg

[57] ABSTRACT

Methods and compositions are provided for performing an assay on whole blood samples. The method is for a determination of an analyte which is a member of a specific binding pair (sbp) consisting of ligand and homologous receptor. The method involves a binding agent for the red blood cells in such sample, a solid bibulous element to which is bound at least one sbp member, and a signal-producing system. The method comprises combining the whole blood sample, the binding agent, and none or, where appropriate, one or more members of the signal producing system. The medium is next contacted with a portion of a solid bibulous element to which is bound one of the members of the specific binding pair to allow the medium to traverse such element (immunochromatography). The solid bibulous element is contacted with any remaining members of the signal producing system. Signal resulting from the signal producing system is detected and is related to the amount of the analyte in the sample.

11 Claims, No Drawings

ASSAY METHOD FOR WHOLE BLOOD SAMPLES

BACKGROUND OF THE INVENTION

1. Field of the Invention

This invention relates to and has among its objects novel methods and compositions for performing an assay for the determination of an analyte in a whole blood sample. The invention finds particular use in immunochromatographic techniques.

The determination of analytes in blood samples has become increasingly more important to medicine, both in diagnosis and therapy. Red blood cells in the sample must be separated prior to performing the assay, which assay is generally performed on blood serum. This is particularly true in assays involving labels, such as enzyme label immunoassays, particularly where a quantitative measurement is to be made. In such determinations one is normally dealing with variable concentrations of the analyte and is normally detecting the difference between two different low level concentrations of analyte. It is a necessary practice to separate red blood cells from the whole blood sample because the cells may inhibit binding which occurs between the sbp members. Furthermore, the cells have enzyme activity which can interfere with the signal produced. Since the quantitative determinations require high precision, the background interference in the assay produced by the presence of red blood cells cannot be tolerated.

An enzyme immunoassay carried out on a whole blood sample thus involves two steps. In the first step, red blood cells are separated from the serum in the whole blood sample. This separation generally involves a centrifugation where the cells settle at the bottom and the serum may be separated by decantation or other method. The separation of the red blood cells from the serum is carried out generally at the site at which the whole blood sample is taken. Following the separation, the serum is transferred to an assay area. Because of the separation step involved, it is necessary to take a relatively large sample of whole blood from a patient, generally on the order of approximately 0.1 to 5.0 ml. Since the taking of the whole blood sample is an invasive procedure, many doctors are reluctant to order assays on a routine basis. A further complicating problem is that most medical offices do not have a blood separator on site. Consequently, the sample must be transferred to an area where the separation of red blood cells from plasma can take place.

There is, therefore, a need for an assay method which can be applied to a whole blood sample of small volume. Such an assay should not have a separate step for removal of red blood cells and should be applicable to a small volume, such as a pin prick drop, of whole blood sample taken from a patient. Such an assay method would allow doctors and others to carry out assays for analytes on a more routine basis

2. Description of the Prior Art

Anderson, *Anal. Biochem.* (1970) 38:175–189 describes the use of cellulose wicks to monitor agglutination reactions. An enzyme chromatographic immunoassay is disclosed in U.S. patent application No. 398,505, filed July 15, 1982, U.S. Pat. No. 4,435,504. Determination of analytes in a particle-containing medium is described in U.S. patent application No. 519,300, filed July 29, 1983, U.S. Pat. No. 4,552,839.

U.S. Pat. No. 4,168,146 describes an immunoassay employing immunochromatography with antigens followed by contacting the immunochromatograph with an aqueous solution containing labeled antibodies. U.S. Pat. No. 4,233,402 describes a homogeneous assay method employing a combination of enzymes, where the substrate of one enzyme is the product of another. Enhanced production of the product is related to the amount of analyte in the assay medium. U.S. Pat. No. 4,275,149 describes the use of particles where combinations of enzymes may be employed, where the presence of the particles enhances the interaction between two enzymes, where the product of one enzyme is the substrate of the other. Enhanced production of the final product due to the presence of the two enzymes bound to the particle as a result of binding of specific binding pair members is related to tne amount of analyte in the assay medium.

Patents concerned with various immobilized reagents on different types of test strips include U.S. Pat. Nos. 3,993,451; 4,038,485; 4,046,514; 4,129,417; 4,133,6391 and 4,160,008. Patents disclosing a variety of methods involving separations of bound and unbound antigen include U.S. Pat. Nos. Re. 29,169; 3,949,064; 3,984,533; 3,985,867; 4,020,151; 4,039,652; 4,067,959; 4,108,972; 4,145,408; and 4,168,148.

SUMMARY OF THE INVENTION

Methods and compositions are provided for detecting the presence of a member of a specific binding pair (sbp) in a whole blood sample. The sbp members consist of ligand and homologous receptor. In the method of the invention the whole blood sample, without separation of red blood cells, is combined in an aqueous buffered medium with a binding agent for the red blood cells in the sample. Where appropriate to the assay protocol, none or one or more members of a signal producing system, which is capable of producing a detectible signal, are included. At least one of the sbp members is substantially uniformly bound to a solid bibulous element. When the assay medium is contacted with a predetermined region of the solid bibulous element, the red blood cells will concentrate in an area on the bibulous element adjacent to the air/liquid interface. Furthermore, the medium will traverse the solid bibulous element. The remaining members of the signal producing system are then combined with the solid bibulous element. The signal produced as a result of the binding of the sbp members is detected and is related to the amount of the sbp member in the sample.

A kit for use in an assay for the determination of the presence of an sbp member in a whole blood sample comprises, in a packaged combination, a binding agent specific for the red blood cells in the sample, a signal producing system which involves at least one label which is bound to an sbp member, a solid bibulous element, and any ancillary materials necessary for carrying out the immunoassay.

DESCRIPTION OF THE PREFERRED EMBODIMENTS

As mentioned above the present method allows for the determination of the presence of an analyte which is an sbp member, in a sample of whole blood suspected of containing the analyte. The present method involves contacting in an aqueous medium a bibulous element, at a predetermined region of the element, with the whole blood sample and a binding agent for red blood cells. The element has an sbp member uniformly bound to the surface of the element. The contacting is carried out so that the sample traverses the element to define a border related to the amount of analyte, and the red blood cells aggregate at an area on the element adjacent to the air-liquid interface i.e., an area on the element at the intersection of the element and the medium. The border is determined by means of a signal producing system which system includes a labeled sbp member.

In the present method the sample is mixed in an aqueous medium with the binding agent. None or, where appropriate, one or more member of a signal producing system is included in the aqueous medium.

Red blood cells are the primary interfering substance in whole blood. Other cellular material may also be classified as interfering substances. This cellular material is present in small amounts in whole blood so that its presence does not result in substantial background interference in an assay. Furthermore, some of this cellular material coaggregates with the red blood cells and is removed from the assay medium during application of the present invention.

Following addition of the binding agent, the sample is contacted with a portion, normally an end, of a solid bibulous element to which is bound an sbp member. The medium diffuses along the bibulous element while the red blood cells are retained at the air/liquid interface. After diffusion is complete, the remaining members of the signal producing system are combined with the solid bibulous element to determine the border which is defined in relation to the amount of analyte in the sample.

Before proceeding further a number of terms will be defined.

Analyte—the compound or composition to be measured, which may be a ligand, which is mono- or polyepitopic, antigenic or haptenic, a single or plurality of compounds which share at least one common epitopic site or a receptor.

Specific binding pair—two different molecules, where one of the molecules has an area on the surface or in a cavity which specifically binds to a particular spatial and polar organization of the other molecule. The members of a specific binding pair are referred to as ligand and receptor (antiligand).

Ligand—any organic compound for which a receptor naturally exists or can be prepared.

Receptor (antiligand)—any compound or composition capable of recognizing a particular spatial and polar organization of a molecule, i.e., epitopic site. Illustrative receptors include naturally occurring receptors, e.g., thyroxine binding globulin, antibodies, enzymes, Fab fragments, lectins and the like.

Ligand Analog—a modified ligand which can compete with the analogous ligand for a receptor, the modification providing means to join a ligand analog to another molecule. The ligand analog will normally differ from the ligand by more than replacement of a hydrogen with a bond which links the ligand analog to a hub or label.

Poly(ligand-analog)—a plurality of ligands or ligand analogs joined together covalently, normally to a hub nucleus. The hub nucleus is a polyfunctional material, normally polymeric, usually having a plurality of functional groups, e.g., hydroxy, amino, mercapto, ethylenic, etc. as sites for linking. The hub nucleus may be water soluble or insoluble, preferably water soluble, and will normally be at least about 35,000 molecular weight and may be 10 million or more molecular weight, but usually under 600,000, more usually under 300,000.

Illustrative hub nucleii include polysaccharides, polypeptides, including proteins, nucleic acids, ion exchange resins and the like.

Signal producing system—the signal producing system may have one or more components, at least one component being conjugated to a specific binding pair member. The signal producing system produces a measurable signal which is detectible by external means, usually the measurement of electomagnetic radiation. For the most part, the signal producing system will involve enzymes and chromophores, where chromophores include dyes which absorb light in the ultraviolet or visible region, phosphors, fluorescers, and chemiluminescers. For the most part, the signal is conveniently the absorption or emission of electromagnetic radiation, usually in the ultraviolet or visible range.

Label—the label may be any molecule conjugated to another molecule and is arbitrarily chosen as to which molecule is the label. In the subject invention, the labels will be the specific binding pair molecule that is conjugated to a member of the signal producing system.

Binding pair label—a member of a specific binding pair employed for binding its homologous member.

Signal label—a member of the signal producing system whicn is directly or indirectly (through the binding of a specific binding pair) bonded to a binding pair member.

Labeled ligand—the conjugate of the ligand member of the specific binding pair with a member of the signal producing system, either covalently or noncovalently bound, when covalently joined, either joined by a bond, linking group, or hub nucleus. The labeled ligand may have one or more ligands (includes ligand analogs) or one or more labels or a plurality of both, the latter being referred to as poly(ligand analog)-polylabel.

Labeled receptor—the conjugate of receptor with a member of the signal producing system, where the two are bound either covalently or non-covalently, usually covalently by a linking group, where there may be one or more receptors bound to the label, but usually one or more labels bound to the receptor.

Binding agent—a binding agent for red blood cells and capable of aggregating the red blood cells in whole blood. The binding agent should be capable of allowing separation of the red blood cells from the medium by partitioning the red blood cells between a surface and a liquid phase when the medium is contacted with a bibulous element. For example, the binding agent may be an agglutinating agent which causes the red blood cells to adhere to one another, such as, e.g., antibody specific for red blood cells. Other types of aggregating agents are polymeric amino acids such as polylysine, polyarginine, etc., and lectins, such as wheat germ agglutinnin (*Triticum vulgaris*), concanavalin A, etc.

Bibulous element—may be any bibulous absorbant solid material which allows for capillary transport of a liquid away from the interface between the air and the liquid. Various materials include paper, cellulose particles, silica gel, cellulosic beads, and the like. Preferably, the surface is relatively smooth so as to allow for the retention of the aggregated red cells as a sharp band or line at or near the air/liquid interface. The size and shape of the bibulous material may be varied widely considering the purpose of the material namely to retain the aggregated red blood cells and to be a support on which to conduct an assay for an analyte. The surface may have different physical characteristics and can be of different chemical compositions and may be of one or more compositions such as a mixture of compositions or laminates or combinations thereof. Various materials may be employed, the primary considerations being the aggregation of the red blood cells at the air/liquid interface and the ease of conjugating to the surface of the element.

Bibulous element—sbp member conjugate (immunochromatograph)—at least one sbp member is non-diffusively bound to the surface of the bibulous element, either covalently or non-covalently. This may be accomplished according to the techniques described, for example, in U.S. Pat. Nos. 4,168,146 and 4,299,916, which are incorporated herein by reference.

The binding of the sbp member to the surface is in a region which allows for the movement of a liquid across the region with transport of the analyte and, as appropriate, any members of the signal producing system. One or more members of the signal producing system may be non-diffusively bound to the bibulous support, either covalently or non-covalently.

Method

The subject method brings together two different functions into one single step in an assay method, namely, separation of interfering cells, such as red blood cells, from plasma and determination of an analyte. The whole blood sample to be analyzed is combined in an aqueous medium, normally buffered, with the binding agent and none or, where appropriate, one or more members of the signal producing system.

The binding agent is generally employed in an amount sufficient to cause the red blood cells to be partitioned between a surface and a liquid phase when the medium is contacted with a portion of the bibulous element. For agglutinating agents such as antibodies specific for red blood cells, one employs from about 1 to 20 $\mu$l of an antibody solution, containing 0.5 to 20 $\mu$g of specific antibody per about 50 $\mu$l of whole blood. In the case of poly(amino acids) from about 10–200 $\mu$g are employed per about 50 $\mu$l of whole blood. When a lectin is employed as the binding agent, one may use from about 1–50 $\mu$g per about 50 $\mu$l of whole blood.

It is an advantage of the present method that no holding period is required after the sample is combined with tne binding agent. The medium may be contacted with the bibulous element immediately after the sample is mixed with the binding agent. In such a situation the red blood cells bound to the binding agent, aggregate at the air/liquid interface. Alternatively, the medium may be held for a period of about 0.5 to 10 min., preferably 1 to 2 min. Assay performance is not affected by the presence or absence of a holding period.

As mentioned above, in carrying out the method, an aqueous medium will normally be employed. Other polar solvents may also be included, usually oxygenated organic solvents of from 1-6, more usually from 1-4 carbon atoms, including alcohols, ethers and the like. Usually these cosolvents will be present in less than about 40 weight percent, more usually in less than about 20 weight percent.

We have found that the pH for the medium will usually be in the range of about 4-11, more usually in the range of about 6-10. Generally, the pH must be chosen to achieve a significant level of binding between the sbp members. Various buffers may be used to achieve the desired pH and maintain the pH during the determination. Illustrative buffers include borate, phosphate, carbonate, Tris, barbital and the like. The particular buffer employed is not critical to this invention but in individual assays, one buffer may be preferred over another.

The ionic strength will generally vary from about 0.01 to 1.0, preferably about 0.1 to 0.4. One may optimize the pH and ionic strength within the above ranges depending upon the particular assay and agents employed. The ionic strength influences the ability of the red blood cells to be retained at the air/liquid interface.

The temperature during the assay may range from about 4°-37° C., more usually from about 20°-25° C. without affecting the assay performance.

The medium is contacted with a portion, usually an end, of the immunochromatograph. Sufficient time is allowed for the medium front to migrate away from the region of contact and traverse the portion of the immunochromatograph which is not in contact with the aqueous medium. Under the above conditions the cellular material is substantially retained at the air/liquid interface. By the term substantially retained is meant that the red blood cells are retained at the air/liquid interface to a degree sufficient to allow detection of a signal from the signal producing medium in relation to the analyte in the sample with little or no background interference.

Following the diffusion of the medium along the immunochromatograph, any remaining members of the signal producing system are combined with the immunochromatograph. The order of combination of the components of the signal producing system with the bibulous element is dependent upon the particular protocol to be followed.

The concentration of analyte which may be assayed will generally vary from about $10^{-4}$ to $10^{-15}$M, more usually from about $10^{-6}$ to $10^{-13}$M. Considerations such as whether the assay is qualitative, semi-qualitative or quantitative, the particular detection technique and the concentration of the analyte of interest will normally determine the concentration of the other reagents.

The order of addition of the various reagents may vary widely, depending upon the nature of the assay to be performed, tne particular labels, the compound to which the label is conjugated, the nature of the conjugates, the nature of the analyte, and the relative concentrations of the analyte and reagents.

The labeled sbp member may be employed in at least three different ways. For example, two of the ways involve the labeled sbp member being present in tne aqueous medium prior to contact with the immunochromatograph and a third way involves the labeled sbp member (ligand and receptor) being present in a reagent solution used after the aqueous medium has diffused along the immunochromatograph. In the first two approaches either the sbp member-label traverses the immunochromatograph concurrently with the analyte, so as to actually compete with the analyte for available binding sites; or, the sbp member-label does not have an apparent competition and primarily binds in a zone immediately beyond the zone in which the analyte has bound. In one instance, one obtains a zone extending from the initial line of contact of the sample containing solvent with the immunochromatograph to the border of the traversing medium. In the other situation, a border results distinguishing between the zone in which the analyte is bound and the zone which is analyte free.

In the third approach mentioned above, where one has antigenic analytes, the method involves an initial contact with the sample. The sample traverses the immunochromatograph and the immunochromatograph is immersed in a solution containing labeled sbp member, which binds to the antigen. This assay is conventionally referred to as a sandwich assay. Of course, where a hapten is involved, one can provide for a fixed amount of a polyligand, that is, the ligand can be polymerized or conjugated to a hub nucleus, so as to provide for a plurality of determinant sites common to both the haptenic analyte and the polyligand. In effect, one produces an antigen where the extent of travel of the synthetic antigen will be related to the amount of analyte in the sample.

When the immunochromatograph is contacted substantially uniformly, e.g., by immersing, spraying, etc., with a solution containing labeled sbp member, the labeled member will bind to the available determinant sites of the antigen, resulting in a detectable signal defining a region related to tne amount of analyte in the sample. Contact through immersion can be carried out by removing the bibulous element from the aqueous medium and placing it in the solution containing labeled sbp member. Alternatively, the solution containing the labeled sbp member may be added to the aqueous medium containing the immunochromatograph.

Rather than employ an antigen, which acts as a bridge between two antibodies, one can employ one sbp member in the solution with the reciprocal sbp member on the immunochromatograph. After allowing the analyte to traverse the immunochromatograph, the immunochromatograph is contacted, again substantially uniformly, e.g., by immersing, spraying, etc., with a solution of labeled sbp member. The labeled sbp member is complementary to the sbp member bound to the immunochromatograph, so that the labeled sbp member will bind to available binding sites defining the region on the immunochromatograph free of analyte. In this way, the distance the analyte has traversed is indicated by the absence of an observable signal in the region containing the analyte, and the border is defined by the presence of the signal in the region free of the analyte Depending upon the particular protocols, washings may be useful or desirable or may be avoided. Preferred protocols are those which provide for a minimal number of steps with minimal possibility of operator error. Therefore, the devised protocols should minimize both washing and measuring steps, which steps contribute to errors in the assay. The present invention permits the assay of a whole blood sample in a minimal number of steps.

Where the immunochromatograph is not standardized to the extent that variations in conditions may change the distance the analyte traverses, a standard sample can be provided having a known amount of analyte. The analyte sample and the standard can be run at the same time, and a quantitative comparison can be made between the standard sample and the analyte sample. If necessary, more than one standard can be employed, so that the distance traversed can be graphed for the different concentrations and used to quantitate a particular sample.

For the most part, relatively short times are involved for the immunochromatograph. Usually, the traverse of the sample through the immunosorbing zone will take at least 30 sec and not more than 1 hour, more usually from about 1 min to 30 min. The development of the signal will generally range from 30 sec to 30 min, more usually from about 30 sec to 5 min.

In enzyme immunoassays the signal producing system has at least one enzyme and may have one or more other components or one or more substrates. The signal producing system may also include coenzymes. An enzyme or coenzyme may be employed as a label, where the presence of the label on the immunochromatograph provides for a substantial change in signal in the area of the label. Usually, the label will be an enzyme but other labels may be employed.

The label provides for a multiplicity of events in its vicinity by providing for enzyme turnover of a substrate. Thus, the member of the signal producing system which is used as the label will be referred to as the enzymatic signal amplifier and is limited to those members indicated above.

The individual or combination of enzyme labels may be varied widely. The product producing the detectable signal may be a dye, fluorescer or chemiluminescer. The signal may be detected by visual observation, due to absorption, fluorescence, or chemiluminescence. On the other hand, a spectrophotometric measurement, employing measuring absorption, reflectance, fluorescence or chemiluminescence, may be made.

For the most part the enzymes of interest will be oxidoreductases and hydrolases. A large number of enzymes of interest are set forth in U.S. Pat. No. 4,275,149, which is incorporated herein by reference. For combinations of enzymes one enzyme is non-diffusively bound to the immunochromatograph, while the other enzyme is conjugated to an sbp member.

If the label-sbp member conjugate was not combined with the sample, the immunochromatograph is contacted substantially uniformly with a solution having labeled-sbp member conjugate after the sample has traversed the immunochromatograph. Depending on the label and the protocol one or more other members of tne signal producing system may also be included.

In the case of an enzyme-sbp member conjugate the immunochromatograph is contacted with a solution of enzyme-sbp member conjugate and substrate, optionally with a scavenger. In this situation, an enzyme is bound to the immunochromatograph, which enzyme is related to the enzyme bound to sbp member by the substrate of one being the product of the other. The enzyme-sbp member conjugate will normally be in an aqueous buffered solution and may be present in substantial excess of available binding sites. The pH range and buffers have been previously considered. After a sufficient time for the enzyme-sbp member conjugate to bind either to ligand or receptor and for color to form, the immunochromatograph is removed from the solution.

By having the two enzymes, a step in the protocol is eliminated since the enzyme-sbp member conjugate and substrate may be combined in the same solution without reaction prior to contacting the immunochromatograph.

After contacting the enzyme-sbp member conjugate and tne immunochromatograph, the immunochromatograph is developed by immersion in a substrate solution. In this case an enzyme may or may not be bound to the immunochromatograph.

With the coenzyme label, the developer solution will usually contain (1) one or more enzymes to provide for regeneration of the coenzyme and (2) substrate. Since the enzymatic reaction requires the coenzyme, the enzyme and substrate may be combined as a single developer reagent without any reaction prior to contact with the immunosorbing zone.

The substrates will vary with the enzymes and are normally in substantial excess, so as not to be rate limiting. The aqueous solution will usually be appropriately buffered for the enzyme system and may include a scavenger for tne product of the enzyme which is the substrate of the other enzyme, e.g., catalase for hydrogen peroxide from uricase.

The immunochromatograph is contacted with the developer solution for a sufficient time to produce sufficient detectable signal producing compound so as to define the region of the immunochromatograph in which tne analyte is bound. Once the detectable signal has been produced, the distance from one end of the chromatograph may be measured as a quantitative measure of the amount of analyte in the sample.

While some distortion may be observed at the border, in most situations the border is reasonably well defined, so that changes in concentration of factors of two or less in the $\mu g$ to pg range can be detected with a wide variety of analytes. Thus, by employing an appropriate dye precursor as a substrate, the amount of an analyte can be quantitatively determined by visual observation with a single measurement (the sample) by the user and a protocol which is relatively insensitive to interference.

Materials

The components employed in the subject method are: the bibulous support, the binding agent, the sbp member conjugates, (which include the sbp member and the label), the sbp member bound to the bibulous element in a particular zone (immunosorbing zone) on the immunochromatograph, remaining members of the signal producing system, sample containing analyte, and, as appropriate, polyligand or polyvalent receptor.

Analyte

The ligand analytes of this invention are characterized by being monoepitopic or polyepitopic, while the receptor analytes may have a single or plurality of binding sites. The polyepitopic analytes will normally be poly (amino acids), i.e., polypeptides and proteins, polysaccharides, nucleic acids, and combinations thereof. Such combinations or assemblages include bacteria, viruses, chromosomes, genes, mitochondria, nuclei, cell membranes and the like.

For the most part, the polyepitopic ligand analytes employed in the subject invention will have a molecular weight of at least about 5,000, or usually at least about 10,000. In tne poly(amino acid) category, the poly (amino acids) of interest will generally be from about 5,000 to 5,000,000 molecular weight, more usually from about 20,000 to 1,000,000 molecular weight, and among hormones of interest, about 5,000 to 60,000 molecular weight.

An extensive listing of useful ligands may be found in U.S. Pat. No. 4,275,149, the disclosure bridging columns 12 to 17, which disclosure is incorporated herein by reference.

The monoepitopic ligand analytes will generally be from about 100 to 2,000 molecular weight, more usually from about 125 to 1,000 molecular weignt. The analytes of interest includes drugs, metabolites, pesticides, pollutants, and the like.

A large number of analytes of interest are listed in U.S. Pat. No. 4,275,149, columns 17 and 18, which disclosure is incorporated herein by reference.

For receptor analytes, the molecular weights will generally range from about $10^4$ to $2 \times 10^8$, more usually from about $3 \times 10^4$ to $2 \times 10^6$. For immunoglobulins, IgA, IgD, IgE, IgG and IgM, the molecular weights will generally vary from about 160,000 to about $10^6$. Enzymes will normally vary from about 10,000 to 600,000 daltons. Natural receptors vary widely, being generally at least about 25,000 molecular weight and may be $10^6$ and higher, including such materials as avidin, thyroxine binding globulin, thyroxine binding prealbumin, transcortin, membrane surface proteins, etc.

Where a ligand is conjugated to another molecule or support, frequently the ligand will be modified to provide for a particular functional group at a particular site. This modification produces a product referred to as a ligand analog. U.S. Pat. No. 4,275,149 also has an extensive description of ligand analogs, bridging columns 18 and 19, which description is incorporated herein by reference.

Binding Agent

Any binding agent specific for red blood cells can be employed in the present method provided that such agent does not interfere with the assay such as by causing the sbp members to aggregate or by interfering with the binding of the sbp members. The binding agent should allow for separation between the analyte and the red blood cells by partitioning the red blood cells between a surface and a liquid phase.

One group of binding agents comprises agglutinating agents which cause the red blood cells to adhere to one another. Exemplary of agglutinating agents are antibodies specific for red blood cells. For example, for human red blood cells one may raise antibodies to such cells in a non-human host according to conventional techniques. Alternatively, one may produce monoclonal antibodies to human red blood cells using approaches known in the art.

One may also employ as the binding agent other materials specific for the red blood cells. Exemplary of such materials are polymeric amino acids such as polylysine, polyarginine, etc., and lectins such as wheat germ agglutinnin, concanavalin A, etc.

Immunochromatograph

The immunochromatograph involves a bibulous element providing liquid travel through capillarity, a nondiffusively bound sbp member, and may also include one or more members of the signal producing system.

A wide variety of elements may be used of different dimensions, particularly thicknesses, different materials and different shapes. For the most part, the shape will be elongated, conveniently a rectangular strip. At least a portion of the strip will have a mip uniformly bound to the strip. The size of the strip will be governed to some degree by convenience in handling. Also, the immunosorbing zone must be of sufficient size to be able to accommodate all of the analyte molecules which may be present in the concentration range of interest of the analyte. Where the protocol involves binding of both analyte and labeled sbp member, then the immunosorbing zone must include capacity for both the analyte and labeled sbp member.

A wide variety of bibulous elements may be used, which include both natural and synthetic polymeric materials, particular cellulosic materials, such as fiber containing papers, e.g., filter paper, chromatographic paper, etc., synthetic or modified natural occurring polymers, such as cross-linked dextran, acrylates, etc., either used by themselves or in conjunction with a ceramic material, such as silica.

The thickness of the immunochromatograph will generally vary from about 0.05 mm to about 2 mm, more usually being about 0.1 mm to 0.5 mm, preferably from about 0.2 mm to about 0.4 mm. The structure of the paper may be varied widely and includes fine, medium fine, medium, medium coarse and coarse. The surface may be varied widely with varying combinations of smoothness and roughness combined with hardness and softness.

The immunochromatograph may be supported by a variety of inert supports, such as Mylar, polystyrene, polyethylene, or the like. The supports can be used as a backing spaced from the immunochromatograph, edging, or other structure to enhance the mechanical integrity of the immunochromatograph.

The immunochromatograph may be coated with a wide variety of materials to provide for enhanced properties. Coatings may include protein coatings, polysaccharide coatings, sugars or the like, which are used particularly to enhance the stability of the materials conjugated to the support. These compounds may also be used for improved binding of the materials, such as the sbp member or signal producing system member bound to the immunochromatograph.

The immunochromatograph may be activated with reactive functionalities to provide for covalent bonding of the organic materials to be conjugated to the surface. Various techniques which may be used to activate the immunochromatograph's bibulous surfaces, including functionalization with an acyl group, e.g., carbonyldiimidazole, treatment with cyanogen bromide or difunctional agents such as glutaraldehyde, succinic acid, etc. Methods for binding of a wide variety of materials to a bibulous surface may be found in the literature. See for example, U.S. Pat. No. 4,168,146.

The amount of sbp member which is bound to the surface will vary depending upon the size of the surface and the amount required to bind all of the analyte and, as required, labeled sbp member. Generally, the amount of sbp member will range from about $10^{-5}$ to $10^{-14}$ moles/cm$^2$, more usually from about $10^{-7}$ to $10^{-12}$ moles/cm$^2$. The number of moles per unit area will be varied in order to insure that there is sufficient discrimination in the concentration range of interest for the distance traversed by the analyte.

In a preferred embodiment, a signal producing system member is non-diffusively bound to the surface of the bibulous element. Particularly, an enzyme is bound to the surface which will interact with the labeled sbp member, where the label is another enzyme. The relationship of the enzymes will be discussed in the description of the signal producing system.

Both the sbp member and the signal producing system member may be bound to a variety of surfaces by adsorption, rather than covalent bonding. This will involve contacting the bibulous element with the solution containing the sbp member and/or signal producing member. The solution may be contacted with the immunochromatograph by immersing, spraying, painting, or other technique which will provide uniformity.

Generally, relatively large sheets will be used which may then be cut to the appropriate dimensions.

Signal Producing System

The signal producing system will, for the most part, involve the production of a detectable signal involving the absorption or emission of electromagnetic radiation, particularly light in the ultraviolet and visible region, more particularly radiation having a wavelength in the range of about 400 to 800 nm. Because of the nature of the immunochromatograph, in order to have a detectable signal, it is necessary that there be a sufficient concentration of the label over a unit area. Therefore, for the most part, individual labels will not be sufficient to provide the desired sensitivity. To that extent, means must be provided for the generation of a plurality of detectable molecules associated with a single labeled sbp member, where the signal-generating label which provides the means for such generation does not interfere with the traversing of the labeled sbp member througn the immunosorbing zone. Therefore, one employs a label which can produce a large number of molecules which can be detected, such as an enzyme or coenzyme. Amplification is then obtained by the presence of a single label.

An enzyme or coenzyme is employed which provides the desired amplification by producing a product, which absorbs light, e.g., a dye, or emits light upon irradiation or chemical reaction, a fluorescer, or chemiluminescer. A large number of enzymes and coenzymes for providing such products are indicated in U.S. Pat. No. 4,275,149 bridging columns 19 to 23, and U.S. Pat. No. 4,318,980, columns 10 to 14, which disclosures are incorporated herein by reference.

Of particular interest is the use of a combination of enzymes, where the enzymes are related by the product of one enzyme being the substrate of the other enzyme. In this manner, the border between the zones containing the bound analyte and free of analyte is more effectively defined.

A number of enzyme combinations are set forth in U.S. Pat. No. 4,275,149, bridging columns 23 to 28, which combinations can find use in the subject invention. This. disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, e.g., peroxidase, microperoxidase, and cytochrome C oxidase. Additional enzyme combinations may be found in the subject matter incorporated by reference. While the above oxidoreductase combination is preferred, other enzymes may also find use such as hydrolases, transferases, and oxidoreductases other than the ones indicated above.

Illustrative coenzymes which find use include NAD[H]; NADP[H], pyridoxal phosphate; FAD[H]; FMN[H], etc., usually coenzymes which combine with oxidoreductases. For a number of coenzymes involving cycling reactions see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure is incorporated herein by reference.

By appropriate manipulation or choice of the label sbp member conjugate, the receptors, the bibulous support and the conditions employed in performing the assay, two different protocols of the subject invention can be performed where the analyte and enzyme-sbp member are applied to the immunochromatograph in the same solution. In one protocol, the region of the immunosorbing zone traversed by the analyte is observable due to production of the detectable signal substantially uniformly throughout the region in which the analyte is present. In the other protocol, the detectable signal is primarily observable at a border related to the region in the immunosorbing zone occupied by the analyte.

The different results may be related to different binding constants, rates of travel, adsorption or the like, of the label-sbp member conjugate as compared to the analyte. The variations can be achieved by varying the number of sbp members, particularly haptenic analytes, bound to the labels, varying the binding specificity of receptors bound to the bibulous element e.g. by preparing antibodies to an immunogen having one linking group between the hapten analyte and antigen and employing a different linking group with the label-hapten analyte conjugate, varying the solvent and/or support to vary the Rf factors, or other techniques.

As a result of the use of two enzymes in the signal producing system with one enzyme as a label, a simplified protocol can be employed, also a strong detectable signal is obtained providing for accurate delineation of the front to which the analyte progressed. By having the product of the enzyme bound to the bibulous element be the substrate of the enzyme conjugated to the sbp member, a sharp, rapid and uniform development of the detectable signal is observed on the immunochromatograph. Furthermore, one establishes a high localized concentration of substrate for tne enzyme bound to the immunochromatograph, so as to encourage the rapid deposit of the detectable signal producing compound at the surface.

Tne invention offers many advantages over tne methodology of the prior art. The primary advantage of the present invention is that the assay may be applied to a whole blood sample. Thus, there is no need to first separate plasma from red blood cells prior to performing the assay.

The assay of the present invention can be performed in medical offices by non-specially trained personnel without the use of sophisticated equipment for separating red blood cells from whole blood samples. A further advantage of the present invention is that a very small sample of whole blood is necessary to perform an assay. Generally, one or two drops of blood, approximately 50 to 150 microliters, are all that are necessary to conduct the assay. Thus, the present invention avoids the invasive procedure of taking much larger whole blood samples to perform assays. A sufficient sample may be obtained merely by pricking a finger to obtain a blood drop.

Kits

As a matter of convenience, the immunochromatograph can be provided as a kit, i.e., a packaged combination with other reagents for combination with a sample in assaying for an analyte. The components of the kit will be provided in predetermined ratios. Where two enzymes are involved, the other reagents will include enzyme labeled mip, substrate for the enzyme bound to the bibulous element, any additional substrates and cofactors required by the enzymes, and the dye precursor, which provides the detectable chromophore or fluorophore. With the coenzyme label the coenzyme labeled member and appropriate enzyme(s) including the dye precursor will be included. In addition other additives may be included, such as stabilizers, buffers, and the like. The relative amounts of tne various reagents may be varied widely, to provide for concentrations in solution of the reagents which substantially optimize tne sensitivity of the assay. Particularly, the reagents may be provided as dry powders, usually lyophilized, including excipients, which on dissolution will provide for a reagent solution having the appropriate concentrations for combining with the sample.

EXAMPLES

The following examples are offered by way of illustration and not by way of limitation.

The following abbreviations are used hereafter: h-hour HRP—horse radish peroxidase; NHS—N-hydroxy succinimide; EDCA—ethyl dimethylaminopropyl carbodiimide; DMF—dimethyl formamide; BSA—bovine serum albumin. Temperatures not otherwise indicated are Celsius, while parts are by weight except for mixtures of liquids which are by volume.

EXAMPLE 1

Preparation of HRP-Oxyamine

To 5 ml of 10 mg/ml horse radish peroxidase in 5 mM sodium acetate, pH 4.5 buffer, was added 50 ml 0.2 M sodium periodate and the mixture stirred for 30 min, followed by chromatography on a G-50 Sephadex column, eluting with 2 mM sodium acetate buffer, pH 4.5. The protein fractions were pooled to 29 ml, the mixture cooled to 4° C. and 2.9 ml of 0.2M 2,2'-oxy-bis-ethylamine in 0.5M carbonate buffer, pH 9.5 at 4° C. added. The pH of the mixture was adjusted to 9.5 with 1N sodium hydroxide, stirred for 2 h and 3.52 ml of a 4 mg/ml sodium borohydride-water solution added and the mixture allowed to react for 3 h, followed by chromatography through a Sephadex ® G-50 column.

The above procedure was repeated using 400 mg of HRP and 3.5 g of 2,2'-oxy-bis-ethylamine. No significant change in enzyme activity was observed between the native amine and the modified amine, which has about four additional amino groups.

EXAMPLE 2

Preparation of immunochromatograph

A sheet (185×230 mm) of Whatman 31ET paper was immersed in 1.8 l. pyridine, 0.2M in carbonyldiimidazole and the mixture was gently stirred for one hour at room temperature. Additional sheets were activated in the same activating solution. Each sheet was then washed with 300 ml tetrahydrofuran and air dried with an air gun over about 20 sec.

A solution (100 ml) of antitheophylline (2 mg/ml) in bicarbonate buffer, pH 9.5 (70 mM NaHCO$_3$ and 30 mM Na$_2$CO$_3$) was placed in a tray. A sheet of paper prepared as above was placed in the tray and was blotted with the above antibody solution. After 1 h, 500 ml of ethanolamine was added to the tray. After an additional hour the sheet was removed from the tray and washed 2 times with 500 ml of a buffer containing 100 mM NaH$_2$PO$_4$, pH 7.0, and 200 mM NaCl. The sheet was then washed 1 time with 500 ml of deionized water.

Following the above washings the sheet was soaked for about 20 min. in 250 ml of aqueous 0.5% polyvinyl-alcohol. The sheet was removed from the polyvinylal-cohol solution and was blotted and tunnel-dried for 5 min. at 65° C.

EXAMPLE 3

Conjugation of Theophylline and HRP

Into a reaction flask was introduced 8.1 mg of 1-methyl-3-(3'-carboxypropyl)xanthine, 3.8 mg of NHS, 6.7 mg EDAC and 125 μl DMF and the mixture allowed to stand overnight at room temperature.

To four-1.3 ml samples of HRP-oxyamine (1 mg) in 0.1M sodium carbonate, pH 9.0, was added varying amounts of the ester prepared above to provide for preparations having mole ratios of theophylline to HRP of 400, 200, and two of 100 each. Into the first reaction mixture (400 mole ratio) was added 0.217 ml of DMF and 66 μl of the above ester in 8.25 μl increments over a period of about 2 h. Into the second reaction mixture (200 mole ratio), 0.238 ml of DMF was added and 33 μl of tne ester added incrementally in 8.25 μl increments. Into the third reaction mixture (100 mole ratio), 0.24 ml of DMF was added and 16.5 μl of the ester added in 8.2 μl increments, while in the final reaction mixture (100 mole ratio), no DMF was added, and 8.25 μl of the ester was added in 2.1 μl increments. During the addition, the temperature was maintained at 4°, and the mixture then allowed to stand overnight at 4°.

The reaction mixtures were then worked up by chromatography on G-25 Sephadex ® with standard buffer. Folin and UV spectroscopic analysis indicated theophylline/HRP ratios of 6.9, 4.0, 1.6 and 2.1, respectively.

In carrying out an assay, whole blood samples (10 μl each) were combined with theophylline such that the respective concentrations therein were 2% blood suspension with 0, 2.5, 10, 20, and 40 μg/ml of theophylline, respectively, in an aqueous medium which further contained 0.2 μg/ml of the conjugate of Example 3, 100 μg/ml of glucose oxidase, 1 mg/ml of BSA, and 5 μl of antibody for human red blood cells.

The sheet prepared in Example 2 was previously cut into strips 6.5×90 mm. The end of a strip (about 5 mm) was dipped into each of the above samples.

After 10 min. a development solution (8 ml) containing 400 μg/ml 4-chloro-1-naphthol which solution was 50mM in glucose, 0.1M sodium phosphate, 0.2M Nacl, pH 7.0, was added to each sample. The distance from the bottom of the strip to the color front was determined for the samples having differing concentrations of theophylline.

For purposes of comparison (Control), the above procedure was repeated except that no whole blood samples were added to the theophylline solutions.

The results are summarized in Table 1. An average value for two runs is given.

TABLE 1

| Theophylline Concentration (μg/ml) | Height (mm) 2% Whole Blood | Control |
|---|---|---|
| 0 | 18 | 18.5 |
| 2.5 | 24.5 | 23 |
| 5 | 31.5 | 31.5 |
| 10 | 39.5 | 42 |
| 20 | 47.5 | 50.5 |

TABLE 1-continued

| Theophylline Concentration (μg/ml) | Height (mm) 2% Whole Blood | Control |
|---|---|---|
| 40 | 58 | 57.5 |

The above results demonstrate that an accurate assay for the theophylline may be carried out on a whole blood sample in accordance with the present invention without a separate step of removing interferring red blood cells.

What is claimed is:

1. A method for determining an analyte in a whole blood sample, said analyte being a member of a specific binding pair ("sbp member") selected from the group consisting of ligand and homologous receptor, which method comprises— contacting in an aqueous medium (A) a bibulous element, at a predetermined region of said element, said element having an sbp member substantially uniformly bound to the surface thereof with (B) a whole blood sample and (C) a binding agent for red blood cells present in said whole blood sample whereby said medium traverses said element to define a border related to the amount of analyte and said red blood cells aggregate at an area on said element adjacent to the air-liquid interface; and determining said border by means of a signal producing system, which system includes a labeled sbp member.

2. The method of claim 1 wherein the binding agent is an agglutinating agent.

3. The method of claim 1 wherein the binding agent is antibody specific for red blood cells.

4. The method of claim 1 wherein the binding agent is a lectin.

5. The method of claim 1 wherein the binding agent is a polymeric amino acid.

6. The method of claim 1 wherein the binding agent is polylysine.

7. The method of claim 1 wherein the pH of said medium is in the range of about 6–10.

8. The method of claim 1 wherein the ionic strength of said medium is in the range of about 0.1–0.4.

9. A method for detecting the presence of a member of a specific binding pair ("sbp member") in a whole blood sample, said sbp member selected from the group consisting of ligand and homologous receptor, where said method involves (1) a binding agent for red blood cells in said sample; (2) a solid bibulous element to which is bound at least one sbp member; and (3) a signal producing system capable of producing a detectable signal, the members of which include at least one label which is bound to an sbp member, said method comprising:

(a) combining in an aqueous medium a whole blood sample, a binding agent for aggregating red blood cells in said sample, and fewer than all the members of the signal producing system, (b) contacting a portion of said bibulous carrier with said aqueous medium to allow said medium to diffuse along said bibulous element and said aggregated red blood cells to concentrate in an area on said element adjacent the air/liquid interface, (c) contacting said bibulous element with any remaining members of the signal producing system, and (d) detecting the signal as a result of said signal producing system, wherein said signal is related to the amount of said sbp member in said sample.

10. The method of claim 9 wherein the binding agent is antibody specific for said red blood cells.

11. A kit for use in a method for determining an analyte in a whole blood sample, said analyte being a member of a specific binding pair ("sbp member") selected from the group consisting of ligand and homologous receptor, which method comprises— contacting in an aqueous medium (a) a bibulous element, at a predetermined region of said element, said element having an sbp member substantially uniformly bound to the surface thereof with (b) said whole blood sample and (c) a binding agent for red blood cells present in said whole blood sample;

whereby said medium traverses said element to define a border related to the amount of analyte and said red blood cells aggregate at a region on said element corresponding to the air-liquid interface; and determining said border by means of a signal producing system, which system includes a labeled sbp member;

said kit comprising in a packaged combination in predetermined ratios for combination with said sample according to said method, (a) a binding agent specific for said red blood cells,
(b) a bibulous element to which is bound at least one sbp member, and
(c) a signal producing system capable of producing a detectable signal in relation to the amount of analyte present in said sample.

* * * * *